(12) United States Patent
Kinoshita et al.

(10) Patent No.: US 10,010,661 B2
(45) Date of Patent: Jul. 3, 2018

(54) SLIDE DEVICE, MECHANICAL SEAL, PUMP AND AUXILIARY ARTIFICIAL HEART SYSTEM

(71) Applicant: SUN MEDICAL TECHNOLOGY RESEARCH CORPORATION, Suwa-shi, Nagano (JP)

(72) Inventors: Hisa Kinoshita, Nagano (JP); Tomoya Kitano, Nagano (JP); Keiichiro Kaneshima, Nagano (JP)

(73) Assignee: SUN MEDICAL TECHNOLOGY RESEARCH CORPORATION, Nagano (JP)

(*) Notice: Subject to any disclaimer, the term of this patent is extended or adjusted under 35 U.S.C. 154(b) by 63 days.

(21) Appl. No.: 15/119,709

(22) PCT Filed: Dec. 5, 2014

(86) PCT No.: PCT/JP2014/082322
§ 371 (c)(1),
(2) Date: Aug. 17, 2016

(87) PCT Pub. No.: WO2015/125378
PCT Pub. Date: Aug. 27, 2015

(65) Prior Publication Data
US 2017/0049944 A1 Feb. 23, 2017

(30) Foreign Application Priority Data
Feb. 19, 2014 (JP) ................................. 2014-029474

(51) Int. Cl.
*A61N 1/362* (2006.01)
*A61M 1/10* (2006.01)
(Continued)

(52) U.S. Cl.
CPC ............ *A61M 1/1025* (2014.02); *F04D 1/00* (2013.01); *F04D 29/0473* (2013.01);
(Continued)

(58) Field of Classification Search
CPC .... A61M 1/1025; A61M 1/102; A61M 1/101; A61M 1/1017; A61M 1/122; F04D 1/00;
(Continued)

(56) References Cited

U.S. PATENT DOCUMENTS

| 4,927,407 A * | 5/1990 | Dorman .................. F04D 13/06 415/112 |
| 2007/0119246 A1 | 5/2007 | Miyakoshi et al. |
| 2013/0102834 A1 | 4/2013 | Kaneshima et al. |

FOREIGN PATENT DOCUMENTS

| JP | 59-195254 U | 12/1984 |
| JP | 2002-85554 A | 3/2002 |

(Continued)

OTHER PUBLICATIONS

International Search Report in PCT/JP2014/082322, dated Mar. 10, 2015.

*Primary Examiner* — George Manuel
(74) *Attorney, Agent, or Firm* — Hauptman Ham, LLP

(57) ABSTRACT

Provided is a slide device which includes a fixed-side slide member having an annular-shaped first slide surface, and a rotary-side slide member having an annular-shaped second slide surface, with the slide device being configured such that the first slide surface and the second slide surface are positioned opposite to each other, and an outer peripheral side of the fixed-side slide member and an outer peripheral side of the rotary-side slide member are brought into contact with a liquid containing a blood component, and a region where the first slide surface and the second slide surface face each other along the rotary-side slide member, the first slide surface and the second slide surface are brought into contact (Continued)

with each other on an outermost periphery of the opposite-facing region of the first and second slide surfaces.

12 Claims, 7 Drawing Sheets

(51) Int. Cl.
*F04D 29/047* (2006.01)
*F04D 29/06* (2006.01)
*F04D 1/00* (2006.01)
*F04D 29/12* (2006.01)
*A61M 1/12* (2006.01)

(52) U.S. Cl.
CPC ......... *F04D 29/061* (2013.01); *F04D 29/126* (2013.01); *F04D 29/128* (2013.01); *A61M 1/101* (2013.01); *A61M 1/102* (2014.02); *A61M 1/1017* (2014.02); *A61M 1/122* (2014.02); *F05D 2250/192* (2013.01)

(58) Field of Classification Search
CPC .. F04D 29/126; F04D 29/0473; F04D 29/061; F04D 29/128; F16J 15/162; F05D 2250/192
See application file for complete search history.

(56) References Cited

FOREIGN PATENT DOCUMENTS

| | | | |
|---|---|---|---|
| JP | 2005-296528 | A | 10/2005 |
| JP | 2013-85913 | A | 5/2013 |

* cited by examiner

US 10,010,661 B2

SLIDE DEVICE, MECHANICAL SEAL, PUMP AND AUXILIARY ARTIFICIAL HEART SYSTEM

RELATED APPLICATIONS

The present application is a National Phase entry of International Application No. PCT/JP2014/082322, filed Dec. 5, 2014, which claims priority of Japanese Application No. 2014-029474, filed Feb. 19, 2014.

TECHNICAL FIELD

The present invention relates to a slide device, a mechanical seal, a pump and an auxiliary artificial heart system.

BACKGROUND ART

A pump which adds a moving force to a liquid is popularly used in various fields. Conventionally, as a pump which adds a moving force to a blood, there has been known a blood pump used in an auxiliary artificial heart system (see patent literature 1, for example). "auxiliary artificial heart system" is a system which substitutes for heart function in order to sustain a life of a patient until he receives heart implantation.

FIG. 9A and FIG. 9B are cross-sectional views showing a conventional blood pump 900. FIG. 9A is a cross-sectional view of the blood pump 900, and FIG. 9B is a view showing a range indicated by symbol A in FIG. 9A in an enlarged manner.

As shown in FIG. 9A, the conventional blood pump 900 includes a slide device 901.

The slide device 901 is a slide member which includes: a fixed-side slide member 912 having an annular-shaped first slide surface 914; and a rotary-side slide member 922 having an annular-shaped second slide surface 924, wherein the first slide surface 914 and the second slide surface 924 are configured to oppositely face each other. The slide device 901 is used in a state where an outer peripheral side of the fixed-side slide member 912 and an outer peripheral side of the rotary-side slide member 922 are brought into contact with blood. The slide device 901 is also a constitutional element of a mechanical seal.

The conventional blood pump 900 includes, besides the slide device 901, a fixed part 910, a rotary portion 920, a rotary drive part 930, and a liquid circulation path 940.

The fixed-side slide member 912 is also a member which forms the fixed part 910.

The rotary-side slide member 922 is also a member which forms the rotary part 920.

The rotary part 920 includes, besides the rotary-side slide member 922, an impeller 926 and a rotary shaft 928.

The liquid circulation path 940 is a path through which a predetermined liquid which performs functions such as lubrication, cooling and maintenance of a seal performance in the blood pump 900 is made to circulate. The predetermined liquid is water or a physiological salt solution, for example, and may also be referred to as a cool sealing liquid or a purge liquid.

The liquid circulation path 940 includes a liquid inlet 942, a liquid supply chamber 944, a liquid passing chamber 946, and a liquid outlet 948.

The liquid passing chamber 946 is positioned on an inner peripheral side of the fixed-side slide member 912 and the rotary-side slide member 922. The blood pump 900 is a blood pump of a type which is used in a mode where a predetermined liquid is made to pass through the liquid passing chamber 946.

According to the conventional blood pump 900, with the provision of the slide device 901 having the above-mentioned configuration, the slide device ensures the smooth sliding between the fixed part and the rotary portion and hence, operational stability of the blood pump 900 is enhanced whereby the blood pump 900 can be stably used in sites where the blood pump 900 is required to perform without fail.

CITATION LIST

Patent Literature

PTL 1: JP-A-2005-296528

SUMMARY OF INVENTION

Technical Problem

In the technical field of a blood pump, there has been a demand for further enhancement of operational stability. This demand is not limited to the technical field of the blood pump used in an auxiliary artificial heart system, and is common among technical fields of pumps which treat blood, an aqueous liquid in which a particular component in blood (blood cell component, blood plasma protein or the like) is dispersed (hereinafter being referred to as "liquid containing a blood component"). To meet such a demand, inventors of the present invention have focused their attention on "seal performance" of a slide device of a pump, and have made expensive studies on "seal performance".

The present invention has been made in view of such circumstances, and it is an object of the present invention to provide a slide device which can acquire higher seal performance than a conventional slide device.

It is another object of the present invention to provide a mechanical seal, a pump and an auxiliary artificial heart system which includes the slide device of the present invention.

Solution to Problem

The inventors of the present invention have studied by focusing on the seal performance of the slide device due to the following reasons. In this specification, "seal performance (also referred to as sealing performance or leakage performance)" is performance by which the entrance (leakage) of a liquid (a liquid containing a blood component in the present invention) on an outer peripheral side of a slide member into an inner peripheral side of the slide member is suppressed.

When seal performance of a slide device is low, an amount of a liquid containing a blood component which enters between a first slide surface and a second slide surface is increased and hence, slide resistance becomes unstable. Further, when the seal performance of the slide device is low, an amount of liquid containing a blood component which enters an inner peripheral side of a fixed-side slide member and a rotary-side slide member is also increased thus giving rise to a possibility that power consumption and the frequency of maintenance are increased.

Accordingly, the increase of seal performance of a slide device has been considered as the task to be solved. As the structure for overcoming this task, for example, there has been adopted the structure which is capable of maintaining and enhancing seal performance using a predetermined liquid (cool seal structure, see the above-mentioned blood pump 900).

However, the inventors of the present invention have considered that seal performance of the slide device can be further increased. Accordingly, the inventors of the present invention have made further extensive studies on the configuration by which sealing performance of a slide device can be further increased, and have completed the present invention. The slide device according to the present invention has the following configurations.

[1] A slide device according to the present invention includes:

a fixed-side slide member having an annular-shaped first slide surface; and a rotary-side slide member having an annular-shaped second slide surface, wherein the slide device is configured to be used in a state where the first slide surface and the second slide surface are made to opposedly face each other, and an outer peripheral side of the fixed-side slide member and an outer peripheral side of the rotary-side slide member are brought into contact with a liquid containing a blood component, wherein assuming a region where the first slide surface and the second slide surface opposedly face each other as viewed in a direction along an axis of rotation of the rotary-side slide member as an opposedly facing region, the first slide surface and the second slide surface are brought into contact with each other on an outermost periphery of the opposedly facing region.

In the conventional slide device 901, as shown in FIG. 9B, the first slide surface 914 and the second slide surface 924 are parallel to each other and hence, both slide surfaces are brought into "face" contact with each other on design. However, minute unevenness or irregularity of a shape is generated on both slide surfaces in an actual product and hence, it is extremely difficult to completely bring both slide surfaces into contact.

As a result, in the conventional slide device 901, it is difficult to maintain a uniform contact state between the first slide surface 914 and the second slide surface 924 and hence, it is difficult to increase seal performance beyond a certain level.

On the other hand, in the slide device of the present invention, the first slide surface and the second slide surface are brought into contact with each other on the outermost periphery of the opposedly facing region (for example, see FIG. 3C described later) and hence, both slide surfaces make a "line" contact with each other. In this case, the degree of contact can be controlled more easily than the case where both slide surfaces are brought into "face" contact with each other.

Accordingly, in the slide device of the present invention, the first slide surface and the second slide surface are brought into contact with each other on the outermost periphery of the opposedly facing region and hence, a uniform contact state can be easily maintained over the entire circumference whereby it is possible to provide a slide device capable of acquiring higher seal performance than a conventional slide device.

According to the slide device of the present invention, an amount of a liquid containing a blood component which enters between the first slide surface and the second slide surface can be decreased by increasing seal performance. Accordingly, the slide device of the present invention can acquire more stable slide resistance than the conventional slide device.

According to the slide device of the present invention, an amount of a liquid containing a blood component which enters an inner peripheral side of the fixed-side slide member and the rotary-side slide member can be reduced by increasing seal performance. Accordingly, the slide device of the present invention can suppress the increase of power consumption and the increase of the frequency of maintenance compared to a conventional slide device.

In this specification, "the first slide surface and the second slide surface are brought into contact with each other" does not mean that the first slide surface and the second slide surface are always brought into contact with each other, but means that both slide surfaces are brought into contact with each other when not in use (at the time of manufacture, when in distribution or the like). The slide device of the present invention is configured such that both slide surfaces are brought into contact with each other on the outermost periphery of the opposedly facing region when nothing enters between the first slide surface and the second slide surface. Such a configuration can be realized by applying a load between the fixed-side slide member and the rotary-side slide member using a magnet or a resilient member, for example.

"a region where the first slide surface and the second slide surface opposedly face each other as viewed in a direction along an axis of rotation of the rotary-side slide member" means a region where the first slide surface and the second slide surface overlap with each other as viewed in the above-mentioned direction. When the first slide surface and the second slide surface have the same inner peripheral diameter and the same outer peripheral diameter, the entirety of the first slide surface and the entirety of the second slide surface fall within the opposedly facing region.

"brought into contact with each other on an outermost periphery of the opposedly facing region" means that the first slide surface and the second slide surface are brought into contact with each other only on the outermost periphery of the opposedly facing region on design. In an actual product, there may be a case where portions in the opposedly facing region other than the outermost periphery (for example, portions of the opposedly facing region in the vicinity of the outermost periphery) are also unavoidably brought into contact with each other due to resilient deformation, wear or the like of the slide members. However, such a case is also embraced by the present invention.

In the conventional slide device and the slide device of the present invention, when the rotary-side slide member is being rotated, a liquid (a liquid containing a blood component or the above-mentioned predetermined liquid) enters between the first slide surface and the second slide surface in a thin layer form. In this case, a high pressure is generated in the liquid which enters between both slide surfaces and hence, the entrance of the liquid containing a blood component into the inner peripheral side of the slide device becomes difficult.

The pressure generated in the liquid which enters between both slide surfaces becomes the highest at a position where a distance between both slide surfaces becomes the smallest. Accordingly, in the slide device of the present invention, the position at which the highest pressure is generated in the liquid is the position where both slide surfaces are brought into contact with each other when the blood pump is not used, that is, the outermost periphery of the opposedly facing region.

Accordingly, in the slide device of the present invention, the first slide surface and the second slide surface make a line contact with each other and hence, a uniform contact state between both slide surfaces can be easily maintained over the entire circumference and hence, it is possible to generate a stable pressure in a liquid which enters between both slide surfaces.

According to the slide device of the present invention, the first slide surface and the second slide surface are brought into contact with each other on an outermost periphery of the opposedly facing region and hence, a portion where both slide surfaces are brought into contact with each other, that is, "a portion where the highest pressure is generated in a liquid which enters between both slide surfaces" is disposed as close as possible to the outer peripheral side whereby an amount of an aqueous liquid containing a blood component enters between both slide surfaces can be reduced.

The slide device of the present invention is preferably applicable to a slide device used in a state where a predetermined load is applied between a fixed-side slide member and a rotary-side slide member in a direction along an axis of rotation of the rotary-side slide member (slide device having so-called thrust bearing structure).

In the slide device of the present invention, when an outer peripheral diameter of the first slide surface and an outer peripheral diameter of the second slide surface are equal to each other, the outermost peripheries of both slide surfaces are brought into contact with each other. On the other hand, when the outer peripheral diameter of the first slide surface and the outer peripheral diameter of the second slide surface differ from each other, the outermost periphery of the slide surface having the smaller outer peripheral diameter is brought into contact with the opposedly facing slide surface.

In the present invention, blood from which blood component is obtained is not limited to blood of human, and may be blood of various animals such as mammals other than human, birds, or reptiles.

[2] In the slide device of the present invention, it is preferable that a gap be formed between the first slide surface and the second slide surface on an inner peripheral side of a contact position where the first slide surface and the second slide surface are brought into contact with each other, a size of the gap being increased as a distance toward the inner peripheral side from the contact position is increased, and to express the size of the gap at an innermost periphery of the opposedly facing region along a direction parallel to the axis of rotation of the rotary-side slide member, the size of the gap at the innermost periphery be set to a value which falls within a range of from 0.2 µm to 0.8 µm.

With such a configuration, a sufficient and uniform contact state can be maintained over the entire circumference and, at the same time, it is possible to generate a sufficient pressure in a liquid which enters between both slide surfaces.

The reason the size of the gap on the innermost periphery of the opposedly facing region is set to 0.2 µm or more is as follows. That is, when the size of the gap is less than 0.2 µm, the difference between the size of the gap at the portion where both slide surfaces are brought into contact with each other and the size of the gap at portions other than the portion where both slide surfaces are brought into contact with each other is so small that a sufficiently uniform contact state may not be maintained over the entire circumference. Further, the reason the size of the gap at the innermost periphery is set to 0.8 µm or less is as follows. That is, when the size of the gap is larger than 0.8 µm, the gap becomes so large that a sufficient pressure may not be generated in a liquid which enters between both slide surfaces.

[3] In the slide device of the present invention, it is preferable that an arithmetic average roughness of the first slide surface and an arithmetic average roughness of the second slide surface be set smaller than the size of the gap at the innermost periphery.

With such a configuration, it is possible to suppress a phenomenon that both slide surfaces are brought into contact with each other at a portion other than the outermost periphery of the opposedly facing region. As a result, seal performance can be further increased.

From the above-mentioned viewpoint, the arithmetic average roughness (Ra) of the first slide surface and the arithmetic average roughness (Ra) of the second slide surface may more preferably be half or less of the size of the gap at the innermost periphery, and may be further more preferably one fourth or less of the size of the gap at the innermost periphery.

[4] In the slide device of the present invention, it is preferable that one slide surface out of the first slide surface and the second slide surface be formed in a flat surface shape perpendicular to the axis of rotation of the rotary-side slide member, and the other slide surface out of the first slide surface and the second slide surface be formed in a shape where the more the other slide surface extends toward the outer peripheral side, the more the other slide surface projects toward said one slide surface.

With such a configuration, it is possible to make the first slide surface and the second slide surface approach each other and to bring them into contact with each other in a state where the other slide surface has a so-called outside raised shape.

Assuming that one slide surface is disposed on an upper side, "a shape where the more the other slide surface extends toward the outer peripheral side, the more the other slide surface projects toward one slide surface" may be also understood as a shape where the other slide surface increases a height thereof toward an outer peripheral side (see embodiment 1 and FIG. 3, for example).

To express the other slide surface in the above-mentioned [4] using flatness (also referred to as PV or surface accuracy), it may be understood that the other slide surface has the same flatness as the size of a gap on an innermost periphery of the opposedly facing region (the highest point disposed at the outermost periphery and the lowest point disposed on the innermost periphery).

A surface of the other slide surface between the outermost periphery and the innermost periphery may have fixed obliquity in all places or may have different obliquities depending on places.

[5] In the slide device of the present invention, it is preferable that the first slide surface be formed in a shape where the more the first slide surface extends toward the outer peripheral side, the more the first slide surface projects toward the rotary-side slide member, and the second slide surface be formed in a shape where the more the second slide surface extends toward the outer peripheral side, the more the second slide surface projects toward the fixed-side slide member.

With such a configuration, it is possible to make the first slide surface and the second slide surface approach each other and to bring them into contact with each other in a state where both slide surfaces have a so-called outside raised shape.

Assuming that the rotary-side slide member is disposed on an upper side and the fixed-side slide member is disposed on a lower side, "a shape where the more the first slide surface extends toward the outer peripheral side, the more the first slide surface projects toward the rotary-side slide member" may be also understood as a shape where the first slide surface increases a height thereof toward an outer peripheral side and "a shape where the more the second slide surface extends toward the outer peripheral side, the more the second slide surface projects toward the fixed-side slide member" may be also understood as a shape where the second slide surface decreases a height thereof toward the outer peripheral side (see embodiment 3 and FIG. 5, for example).

A value obtained by adding the flatness of the first slide surface (the highest point disposed on the outermost periphery and the lowest point disposed on the innermost periphery, the same definition being applicable to the second slide surface) and the flatness of the second slide surface becomes equal to the size of the gap on the innermost periphery of the opposedly facing region.

A surface of the first slide surface and a surface of the second slide surface between the outermost periphery and the innermost periphery may have fixed obliquity in all places or may have different obliquities depending on places.

[6] In the slide device of the present invention, it is preferable that one slide member out of the fixed-side slide member and the rotary-side slide member be made of silicon carbide.

Silicon carbide (SiC) is a material which is excellent in hardness, durability and biocompatibility and hence, silicon carbide can be used safely in a liquid containing a blood component. Accordingly, with such a configuration, it is possible to suppress an effect caused by resilient deformation or the like of the slide surface (particularly, the outermost periphery) by increasing hardness and durability of the slide member.

It is preferable that the slide member which is used together with the slide member made of silicon carbide be made of carbon. Carbon is a relatively soft material which is suitable for being used together with silicon carbide. Carbon also exhibits excellent biocompatibility and can be safely used in a liquid containing a blood component.

It is preferable that both the fixed-side slide member and the rotary-side slide member be made of silicon carbide.

In the slide device described in the above-mentioned [6], it is preferable that "affinity treatment" which is the treatment for forming a hydrate of silicon oxide on a slide surface be applied to the slide member made of silicon carbide before the slide member is assembled to the slide device. With such a configuration, the slide surface of the slide member made of silicon carbide has "a hydrate of silicon oxide having high hydrophilicity" due to a tribochemical reaction. Accordingly, "a blood component having hydrophobicity" minimally adheres to the slide surface. As a result, when the slide member is used in a liquid containing a blood component, slide resistance can be reduced.

"affinity treatment" is the treatment which imparts a friction to a slide surface by increasing a load in accordance with predetermined steps. Affinity treatment can be performed, for example, such that a friction is imparted to the slide surface until a change rate of a friction coefficient at a fixed load falls within a predetermined value (for example, 5%) and, thereafter, the load is increased gradually by a predetermined value (for example, 50N) each time. Affinity treatment is performed under water, for example. It is preferable that the maximum load applied in affinity treatment be larger than a load which is applied when the slide device is actually used. That is, it is more preferable that the maximum load be ten times or more as large as the load applied when the slide device is actually used.

[7] In the slide device of the present invention, it is preferable that the slide device be a slide device which is used in a state where a predetermined liquid is made to pass on an inner peripheral side of the fixed-side slide member and on an inner peripheral side of the rotary-side slide member.

With such a configuration, the inner peripheral side of the fixed-side slide member and the inner peripheral side of the rotary-side slide member are filled with a predetermined liquid when in use and hence, seal performance can be further increased.

[8] In the slide device of the present invention, it is preferable that antithrombotic treatment be applied to an outer periphery of the fixed-side slide member and an outer periphery of the rotary-side slide member.

With such a configuration, it is possible to suppress the generation of thrombus or the adhesion of a blood component on the outer periphery of the fixed-side slide member and the outer periphery of the rotary-side slide member.

As antithrombotic treatment, coating treatment using MPC (2-methacryloyloxyethyl phosphorylcholine) polymer may be exemplified.

[9] A mechanical seal of the present invention includes the slide device of the present invention.

The mechanical seal of the present invention includes the slide device of the present invention which can acquire higher seal performance than the conventional slide device and hence, it is possible to provide a mechanical seal which exhibits high seal performance and can acquire a stable slide state.

The mechanical seal of the present invention includes, besides the slide device of the present invention, constitutional elements necessary for the mechanical seal such as a load applying mechanism (for example, a load applying mechanism which uses a magnet) which applies a predetermined load in a direction along an axis of rotation of the rotary-side slide member and a cushion ring.

[10] A pump of the present invention includes the mechanical seal of the present invention.

The pump of the present invention includes the mechanical seal of the present invention and hence, it is possible to provide a pump which can increase operational stability compared to a conventional pump.

It is preferable that the pump of the present invention be a pump which includes a liquid circulation path through which a predetermined liquid (for example, water or a physiological salt solution, the predetermined liquid also being referred to as a cool sealing liquid or a purge liquid) which performs functions such as lubrication, cooling and maintenance of seal function in the inside of the pump is made to circulate. The pump is used in such a manner that the predetermined liquid is made to pass through a liquid passing chamber positioned on an inner peripheral side of the fixed-side slide member and on an inner peripheral side of the rotary-side slide member. In this case, it is preferable that the mechanical seal of the present invention include the slide device described in the above-mentioned [7].

[11] It is preferable that the pump of the present invention be a blood pump.

With such a configuration, the pump of the present invention can increase operational stability compared to a conventional blood pump, and can be used further stably at a place where an operation with certainty is required.

[12] The auxiliary artificial heart system of the present invention includes the blood pump of the present invention.

According to the auxiliary artificial heart system of the present invention, with the provision of the blood pump of the present invention, it is possible to provide a highly reliable auxiliary artificial heart system.

DESCRIPTION OF EMBODIMENTS

Figure 1:
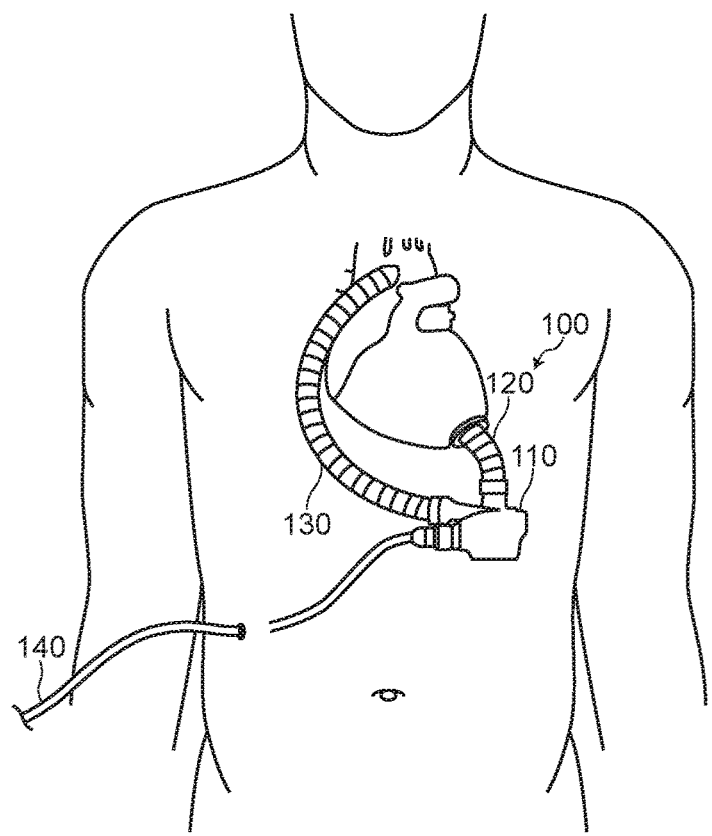
FIG. 1 is a view for describing an auxiliary artificial heart system 100 according to an embodiment 1.

Hereinafter, a slide device, a mechanical seal, a pump and an auxiliary artificial heart system of the present invention are described based on embodiments shown in the drawings.

The respective drawings are schematic views and do not always strictly reflect actual sizes. Particularly, a gap S is indicated considerably larger than an actual gap.

[Embodiment 1]

FIG. 1 is a view for describing an auxiliary artificial heart system 100 according to an embodiment 1.

Figure 2:
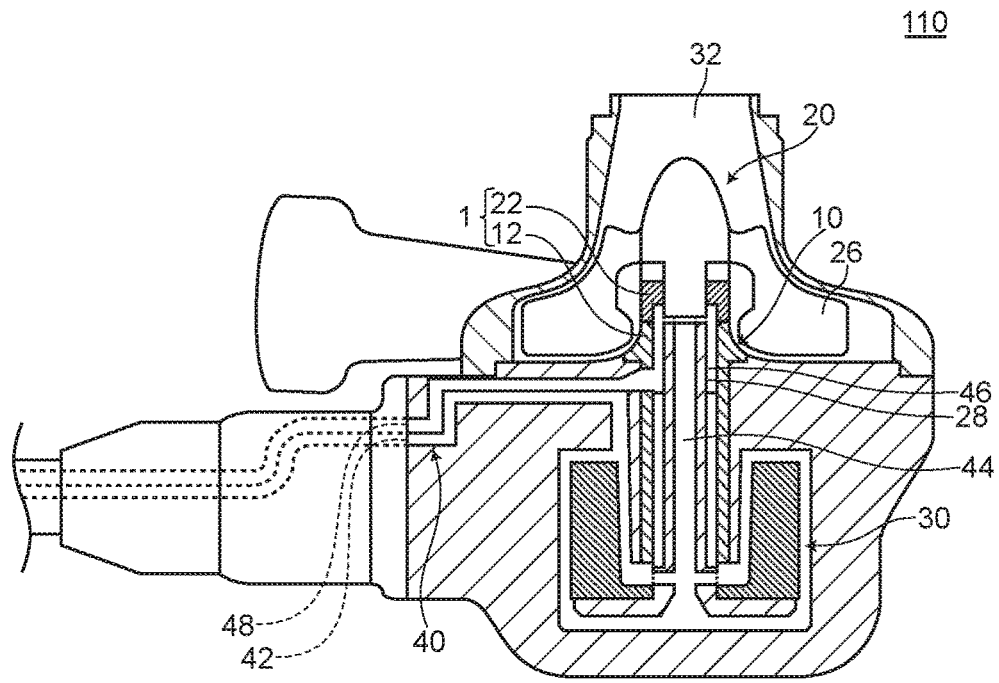
FIG. 2 is a cross-sectional view of a blood pump 110 according to the embodiment 1.

FIG. 2 is a cross-sectional view of a blood pump 110 according to the embodiment 1.

Figure 3A:
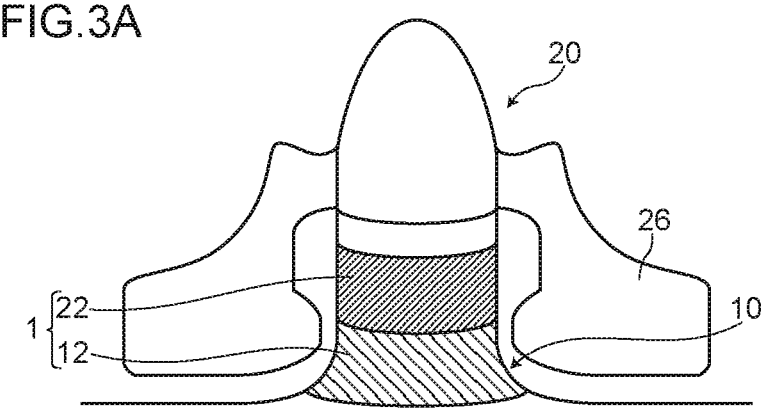
FIG. 3A to FIG. 3C are views for describing the slide device 1 according to the embodiment 1.
Figure 3B:
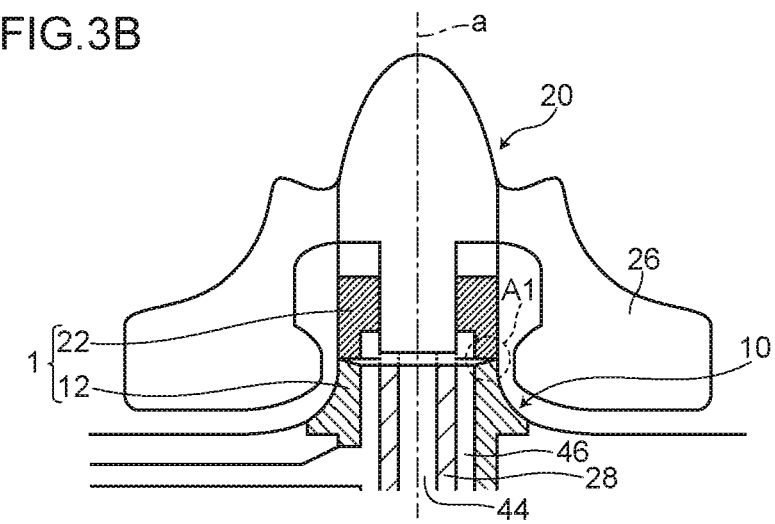
Figure 3C:
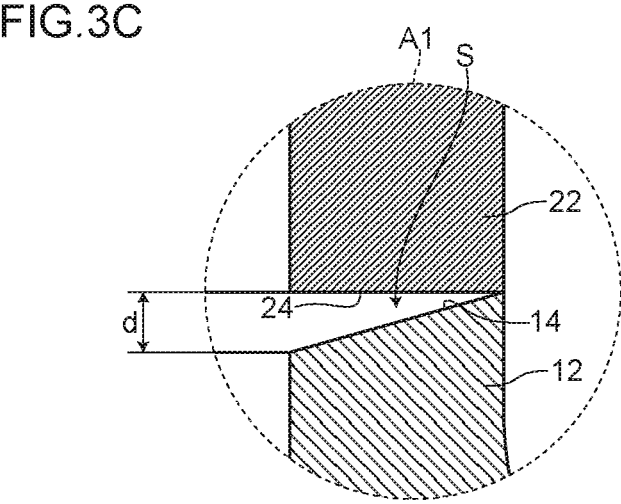

FIG. 3A to FIG. 3C are views for describing the slide device 1 according to the embodiment 1. FIG. 3A is a perspective view of the slide device 1 and constitutional parts around the slide device 1, FIG. 3B is a cross-sectional view of the slide device 1 and the constitutional parts around the slide device 1, and FIG. 3C is a view showing a portion indicated by symbol A1 in FIG. 3B in an enlarged manner.

As shown in FIG. 1, the auxiliary artificial heart system 100 according to the embodiment 1 includes: a blood pump 110 embedded in the inside of a body; artificial blood vessels 120, 130 for connecting the blood pump 110 and a blood vessel of a heart to each other; a controller 150 not shown in the drawing; and a circulation device 160 not shown in the drawing.

The controller 150 is used outside the body of a user of the auxiliary artificial heart system 100, and is connected to the blood pump 110 through a cable 140 when the auxiliary artificial heart system 100 is used.

The circulation device 160 is a device by which a predetermined liquid (for example, water or physiological salt solution) which performs functions such as lubrication, cooling, maintenance of seal performance is made to circulate in the inside of the blood pump 110, and is used outside the body of the user together with the controller 150. The circulation device 160 is connected to a liquid circulation path 40 of the blood pump 110 through the cable 140.

The blood pump 110 according to the embodiment 1 is a pump according to the embodiment. As shown in FIG. 2, the blood pump 110 includes a fixed part 10, a rotary part 20, a rotary drive device 30, a blood pump chamber 32, and the liquid circulation path 40. The blood pump 110 is a pump used so as to allow a predetermined liquid to pass through a liquid passing chamber 46 (described later) which is positioned on an inner peripheral side of a fixed-side slide member 12 and a rotary-side slide member 22.

The fixed part 10 includes the cylindrical fixed-side slide member 12 (a so-called seat ring).

The rotary part 20 includes the rotary-side slide member 22 (a so-called seal ring), an impeller 26 and a rotary shaft 28. The impeller 26 imparts a moving force to a blood. The rotary shaft 28 is connected to the rotary drive device 30. When in use, a rotational force is applied to the rotary shaft 28 by the rotary drive device 30 so that the whole rotary part 20 is rotated.

The fixed-side slide member 12 and the rotary-side slide member 22 form the slide device 1 according to the embodiment 1. The slide device 1 is described later in detail.

The mechanical seal according to the embodiment 1 includes the slide device 1, and suppresses the entrance of a blood into the rotary drive device 30, the liquid circulation path 40 and the like. Although the illustration by drawings, the indication of symbols and the detailed description are omitted, the mechanical seal according to the embodiment 1 includes, besides the slide device 1, constitutional elements necessary for the mechanical seal such as a load applying mechanism (for example, a load applying mechanism which uses a magnet) which applies a predetermined load in a direction along an axis of rotation "a" of the rotary-side slide member 22, and a cushion ring and the like disposed between the rotary-side slide member 22 and the impeller 26.

The rotary drive device 30 generates a rotary force. The rotary drive device 30 includes a rotary motor.

The blood pump chamber 32 is a place where a moving force is applied to blood by the impeller 26.

The liquid circulation path 40 in the blood pump 110 is formed such that a predetermined liquid is made to flow into the blood pump 110 through a liquid inlet 42 and is made to pass through a liquid supply chamber 44 and a liquid passing chamber 46 in this order, and is discharged from a liquid outlet 48. The predetermined liquid has a function of performing lubrication and cooling between the rotary shaft 28 and the fixed part 10. The predetermined liquid also has a function of suppressing the entrance of a blood through a gap formed between the fixed-side slide member 12 and the rotary-side slide member 22, and a function of cleaning a first slide surface 14 and a second slide surface 24 (described later).

The slide device 1 according to the embodiment 1 is described in detail hereinafter.

The slide device 1 includes: as shown in FIG. 3A and FIG. 3B, the fixed-side slide member 12 having an annular-shaped first slide surface 14; and the rotary-side slide member 22 having an annular-shaped second slide surface 24. The slide device 1 is a slide device which is configured to be used in a state where the first slide surface 14 and the second slide surface 24 are made to opposedly face each other, and an outer peripheral side of the fixed-side slide member 12 and an outer peripheral side of the rotary-side slide member 22 are brought into contact with a liquid containing a blood component (blood in the case of the embodiment 1).

In the slide device 1, assuming a region where the first slide surface 14 and the second slide surface 24 oppositely face each other as viewed in a direction along an axis of rotation "a" of the rotary-side slide member 22 as an oppositely facing region, the first slide surface 14 and the second slide surface 24 are brought into contact with each other on an outermost periphery of the oppositely facing region (see FIG. 3B and FIG. 3C). Accordingly, the first slide surface 14 and the second slide surface 24 make a "line" contact with each other.

In the slide device 1, the first slide surface 14 and the second slide surface 24 are brought into contact with each other when not in use. In the slide device 1, when nothing enters between the first slide surface 14 and the second slide surface 24, both slide surfaces are brought into contact with each other on the outermost periphery of the oppositely facing region. Such a configuration can be realized by applying a load between the fixed-side slide member 12 and the rotary-side slide member 22 using a load applying mechanism of a mechanical seal. A magnitude of the load can be set to a value which falls within a range of from 50 gf to 1000 gf, for example.

In the embodiment 1, the first slide surface 14 and the second slide surface 24 have the same inner peripheral diameter and the same outer peripheral diameter on design. Accordingly, although the illustration is omitted, the entirety of the first slide surface 14 and the entirety of the second slide surface 24 fall within the oppositely facing region.

In the slide device 1, the outer peripheral diameter of the first slide surface 14 and the outer peripheral diameter of the second slide surface 24 are equal and hence, the outermost peripheries of both slide surfaces are brought into contact with each other.

The slide device 1 is a slide device which is used in a state where a predetermined load is applied between the fixed-side slide member 12 and the rotary-side slide member 22 in a direction along an axis of rotation "a" of the rotary-side slide member 22 (a so-called slide device having the thrust bearing structure).

The slide device 1 is a slide device which is used in a state where a predetermined liquid is made to pass on an inner peripheral side of the fixed-side slide member 12 and the rotary-side slide member 22 (liquid passing chamber 46, see FIG. 2) when in use.

A gap S is formed between the first slide surface 14 and the second slide surface 24 on an inner peripheral side of a contact position where the first slide surface 14 and the second slide surface 24 are brought into contact with each other. A size of the gap S is increased as a distance toward the inner peripheral side from the contact position is increased (see FIG. 3C). To express a size of the gap S at an innermost periphery of the oppositely facing region along a direction parallel to the axis of rotation "a" of the rotary-side slide member 22, the size "d" of the gap S at the innermost periphery is set to a value which falls within a range of from 0.2 μm to 0.8 μm. The size "d" of the gap S is 0.5 μm, for example.

The arithmetic average roughness (Ra) of the first slide surface 14 and the second slide surface 24 is smaller than the size of the gap on the innermost periphery. For example, the arithmetic average roughness (Ra) is set to a value which falls within a range of from 0.05 μm to 0.10 μm.

The first slide surface 14 is formed in a shape where the more the first slide surface 14 extends toward the outer peripheral side, the more the first slide surface 14 projects toward the second slide surface 24 (so-called outside raised shape) (the first slide surface 14 being the other slide surface). Assuming a side of the second slide surface 24 as viewed from the first slide surface 14 as an upper side, the first slide surface 14 may be also understood as a shape where the first slide surface 14 increases a height thereof toward an outer peripheral side.

To express the first slide surface 14 using flatness, it may be understood that the first slide surface 14 has the same flatness as the size "d" of the gap S on an innermost periphery of the oppositely facing region (for example, 0.5 μm, the highest point disposed on the outermost periphery and the lowest point disposed on the innermost periphery).

A surface of the other slide surface between the outermost periphery and the innermost periphery may have fixed obliquity in all places or may have different obliquities depending on places.

The second slide surface 24 is formed in a flat surface shape perpendicular to the axis of rotation "a" of the rotary-side slide member 22 (one slide surface).

The fixed-side slide member 12 is made of silicon carbide.
The rotary-side slide member 22 is made of carbon.
Antithrombotic treatment is applied to the outer periphery of the fixed-side slide member 12 and the outer periphery of the rotary-side slide member 22. As antithrombotic treatment, coating treatment using MPC (2-methacryloyloxy-ethyl phosphorylcholine) polymer may be exemplified.

Advantageous effects acquired by the slide device 1, the mechanical seal, the pump and the auxiliary artificial heart system according to the embodiment 1 are described hereinafter.

In the slide device 1 of the embodiment 1, the first slide surface 14 and the second slide surface 24 are brought into contact with each other on the outermost periphery of the oppositely facing region and hence, a uniform contact state can be maintained over the whole circumference whereby it is possible to provide a slide device which can acquire higher seal performance than conventional slide devices.

In the slide device 1 of the embodiment 1, an amount of a liquid containing a blood component which enters between the first slide surface and the second slide surface can be reduced by increasing seal performance and hence, the slide device 1 can acquire the more stable slide resistance than conventional slide devices.

In the slide device 1 of the embodiment 1, an amount of a liquid containing a blood component which enters the inner peripheral side of the fixed-side slide member and the rotary-side slide member can be reduced by increasing seal performance and hence, the slide device 1 can suppress the increase of power consumption and the increase of the frequency of maintenance compared to conventional slide devices.

In the slide device 1 of the embodiment 1, the first slide surface 14 and the second slide surface 24 make a line contact with each other and hence, a uniform contact state between both slide surfaces can be easily maintained over the entire circumference and hence, it is possible to generate a stable pressure in a liquid which enters between both slide surfaces.

In the slide device 1 of the embodiment 1, the first slide surface 14 and the second slide surface 24 are brought into contact with each other on an outermost periphery of the oppositely facing region and hence, a portion where both slide surfaces are brought into contact with each other, that is, "a portion where the highest pressure is generated in a liquid which enters between both slide surfaces" is disposed as close as possible to the outer peripheral side whereby an amount of an aqueous liquid containing a blood component which enters between both slide surfaces can be reduced.

In the slide device 1 of the embodiment 1, the size "d" of the gap S at the innermost periphery is set to a value which falls within a range of from 0.2 μm to 0.8 μm and hence, a sufficient and uniform contact state can be maintained over the entire circumference and, at the same time, it is possible to generate a sufficient pressure in a liquid which enters between both slide surfaces.

In the slide device 1 of the embodiment 1, an arithmetic average roughness of the first slide surface 14 and an arithmetic average roughness of the second slide surface 24 are set smaller than the size "d" of the gap S at the innermost periphery and hence, it is possible to suppress a phenomenon that both slide surfaces are brought into contact with each other at a portion other than the outermost periphery of the oppositely facing region. As a result, seal performance can be further increased.

In the slide device 1 of the embodiment 1, the second slide surface 24 (one slide surface) is formed in a flat surface shape perpendicular to the axis of rotation "a" of the rotary-side slide member 22, and the first slide surface 14 (the other slide surface) is formed in a shape where the more the other slide surface (first slide surface 14) extends toward the outer peripheral side, the more the other slide surface (first slide surface 14) projects toward one slide surface (second slide surface 24). With such a configuration, it is possible to make the first slide surface and the second slide surface approach each other and to bring them into contact with each other in a state where the other slide surface has a so-called outside raised shape.

In the slide device 1 of the embodiment 1, the fixed-side slide member 12 is made of silicon carbide. Accordingly, it is possible to suppress an effect caused by resilient deformation or the like of the slide surface (particularly, the outermost periphery) by increasing hardness and durability of the slide member.

In the slide device 1 of the embodiment 1, the slide device 1 is a slide device which is used in a state where a predetermined liquid is made to pass on an inner peripheral side of the fixed-side slide member 12 and the rotary-side slide member 22. Accordingly, the inner peripheral side of the fixed-side slide member and the inner peripheral side of the rotary-side slide member are filled with a predetermined liquid when in use and hence, seal performance can be further increased.

In the slide device 1 of the embodiment 1, antithrombotic treatment is applied to an outer periphery of the fixed-side slide member 12 and an outer periphery of the rotary-side slide member 22. Accordingly, it is possible to suppress the generation of thrombus or the adhesion of a blood component on the outer periphery of the fixed-side slide member and the outer periphery of the rotary-side slide member.

The mechanical seal of the embodiment 1 includes the slide device 1 of the embodiment 1 which can acquire higher seal performance than the conventional slide device and hence, it is possible to provide a mechanical seal which exhibits high seal performance and can acquire a stable slide state.

The pump (blood pump 110) of the embodiment 1 includes the mechanical seal of the embodiment 1 and hence, it is possible to provide a pump which can increase operational stability compared to a conventional pump.

The pump of the embodiment 1 is the blood pump 110. The pump of the embodiment 1 can increase operational stability compared to a conventional blood pump, and can be used further stably at a place where an operation with certainty is required.

The auxiliary artificial heart system 100 of the embodiment 1 includes the blood pump 110 of the embodiment 1. Accordingly, it is possible to provide a highly reliable auxiliary artificial heart system.

[Embodiment 2]

Figure 4A:
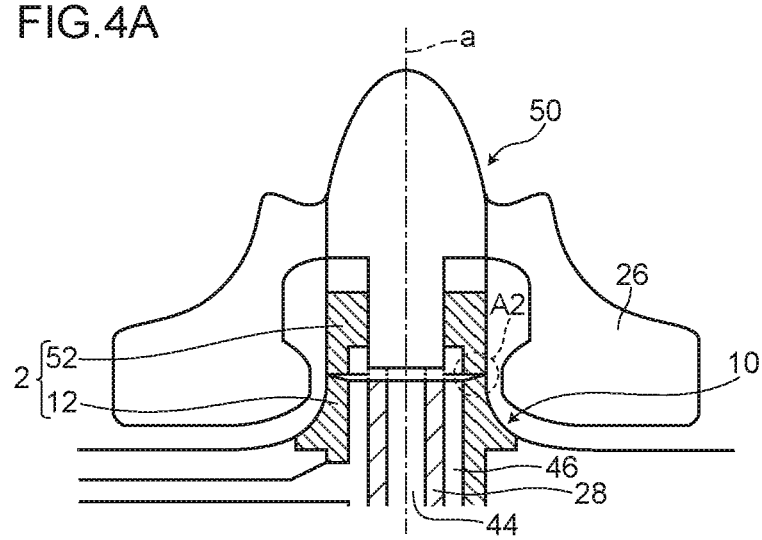
FIG. 4A and FIG. 4B are views for describing a slide device 2 according to an embodiment 2.
Figure 4B:
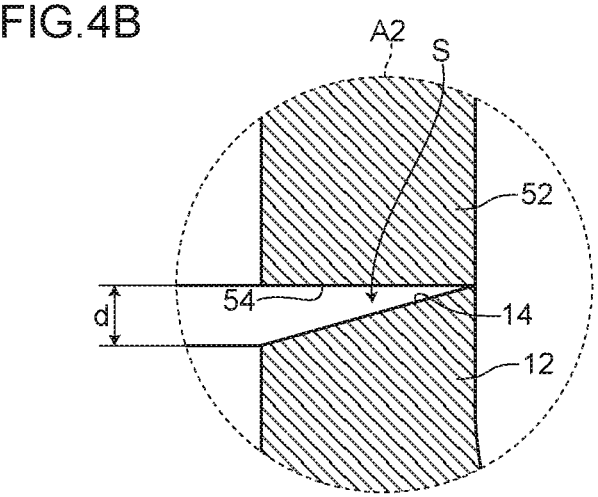

FIG. 4A and FIG. 4B are views for describing a slide device 2 according to an embodiment 2. FIG. 4A is a cross-sectional view of the slide device 2 and the constitutional parts around the slide device 2, and FIG. 4B is a view showing a portion indicated by symbol A2 in FIG. 4A in an enlarged manner.

The slide device 2 according to the embodiment 2 basically has substantially the same configuration as the configuration of the slide device 1 according to the embodiment 1. However, the slide device 2 according to the embodiment 2 differs from the slide device 1 according to the embodiment 1 in the configuration of a rotary-side slide member. That is, in the slide device 2, a rotary-side slide member 52 is made of silicon carbide. Symbol 50 in FIG. 4A indicates a rotary part, and symbol 54 in FIG. 4B indicates a second slide surface.

Although the slide device 2 according to the embodiment 2 differs from the slide device 1 according to the embodiment 1 in the configuration of the rotary-side slide member, a first slide surface 14 and a second slide surface 54 are brought into contact with each other on an outermost periphery of an oppositely facing region and hence, in the same manner as the slide device 1 according to the embodiment 1, a uniform contact state between the first slide surface 14 and the second slide surface 54 can be maintained over the whole circumference whereby it is possible to provide a slide device which can acquire higher seal performance than conventional slide devices.

The slide device 2 according to the embodiment 2 has substantially the same configuration as the configuration of the slide device 1 according to the embodiment 1 other than the configuration of the rotary-side slide member and hence, the slide device 2 according to the embodiment 2 has the advantageous effects acquired by the corresponding configurations out of the advantageous effects acquired by the slide device 1 according to the embodiment 1.

[Embodiment 3]

Figure 5A:
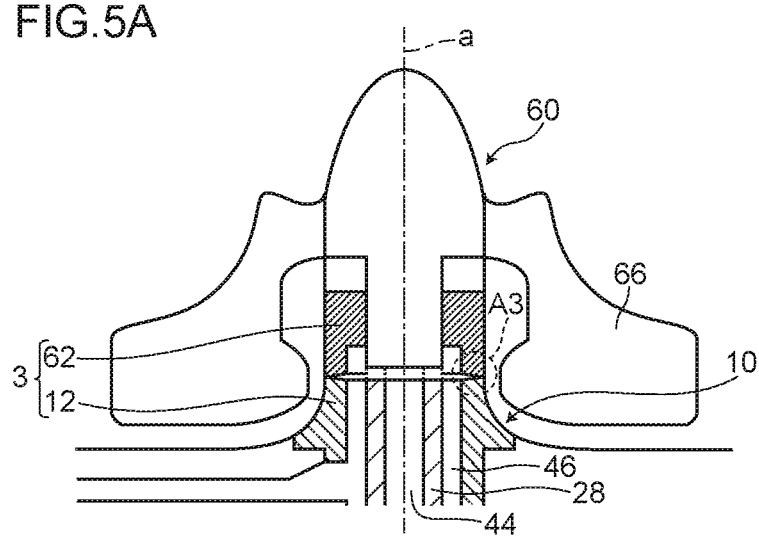
FIG. 5A and FIG. 5B are views for describing a slide device 3 according to an embodiment 3.
Figure 5B:
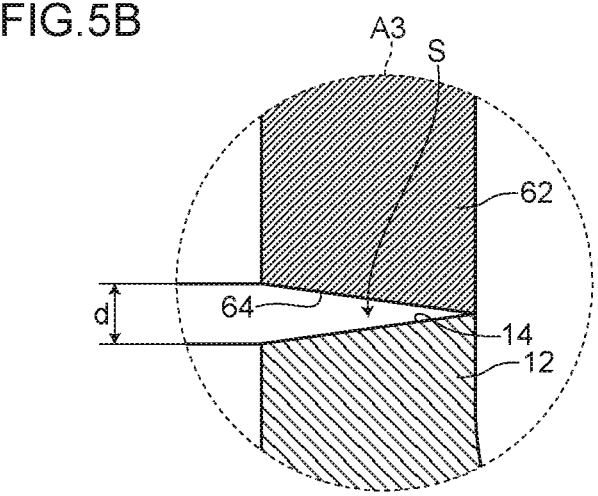

FIG. 5A and FIG. 5B are views for describing a slide device 3 according to an embodiment 3. FIG. 5A is a cross-sectional view of the slide device 3 and the constitutional parts around the slide device 3, and FIG. 5B is a view showing a portion indicated by symbol A3 in FIG. 5A in an enlarged manner.

The slide device 3 according to the embodiment 3 basically has substantially the same configuration as the configuration of the slide device 1 according to the embodiment 1. However, the slide device 3 according to the embodiment 3 differs from the slide device 1 according to the embodiment 1 in the configuration of a second slide surface. That is, in the slide device 3, as shown in FIG. 5A and FIG. 5B, a second slide surface 64 is formed in a shape where the more the second slide surface 64 extends toward the outer peripheral side, the more the second slide surface 64 projects toward the fixed-side slide member 12 (a so-called outside raised shape). Symbol 60 in FIG. 5A indicates a rotary part, and symbol 62 indicates a rotary-side slide member.

Assuming that the rotary-side slide member 62 is disposed on an upper side and the fixed-side slide member 12 is disposed on a lower side, "a shape where the more the first slide surface extends toward the outer peripheral side, the more the first slide surface projects toward the rotary-side slide member 62" may be also understood as a shape where the first slide surface increases a height thereof toward an outer peripheral side and "a shape where the more the second slide surface extends toward the outer peripheral side, the more the second slide surface projects toward the fixed-side slide member 12" may be also understood as a shape where the second slide surface decreases a height thereof toward the outer peripheral side.

A value obtained by adding the flatness of the first slide surface 14 (the highest point disposed on the outermost periphery and the lowest point disposed on the innermost periphery, the same definition being applicable to the second slide surface 64) and the flatness of the second slide surface 64 becomes equal to the size "d" of the gap S on the innermost periphery of the opposedly facing region.

A surface of the first slide surface 14 and a surface of the second slide surface 64 between the outermost periphery and the innermost periphery may have fixed obliquity in all places or may have different obliquities depending on places.

Although the slide device 3 according to the embodiment 3 differs from the slide device 1 according to the embodiment 1 in the configuration of the second slide surface, the first slide surface 14 and the second slide surface 64 are brought into contact with each other on an outermost periphery of the opposedly facing region and hence, in the same manner as the slide device 1 according to the embodiment 1, a uniform contact state can be easily maintained over the entire circumference whereby it is possible to provide a slide device which can acquire higher seal performance than conventional slide devices.

In the slide device 3 of the embodiment 3, the first slide surface 14 is formed in a shape where the more the first slide surface 14 extends toward the outer peripheral side, the more the first slide surface 14 projects toward a rotary-side slide member 62, and the second slide surface 64 is formed in a shape where the more the second slide surface 64 extends toward the outer peripheral side, the more the second slide surface 64 projects toward a fixed-side slide member 12 and hence, it is possible to make the first slide surface and the second slide surface approach each other and to bring them into contact with each other in a state where both surfaces have a so-called outside raised shape.

The slide device 3 according to the embodiment 3 has substantially the same configuration as the configuration of the slide device 1 according to the embodiment 1 other than the configuration of the second slide surface and hence, the slide device 3 according to the embodiment 3 has the advantageous effects acquired by the corresponding configurations out of the advantageous effects acquired by the slide device 1 according to the embodiment 1.

EXPERIMENTAL EXAMPLES

Hereinafter, experimental examples which are carried out for confirming advantageous effects of slide devices of the present invention are described.

Experimental Example 1

Figure 6A:
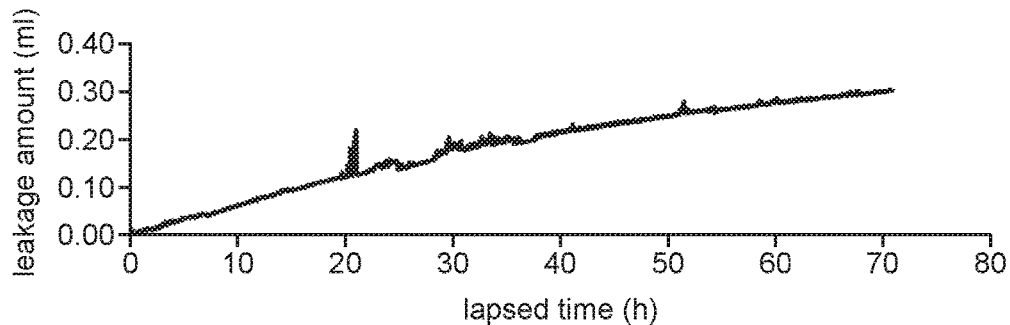
FIG. 6A and FIG. 6B are graphs for describing the difference in seal performance between a slide device according to an experimental example and a slide device for comparison.
Figure 6B:
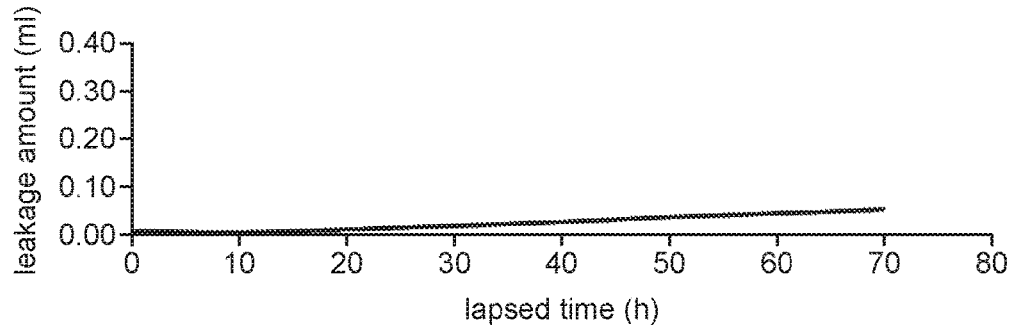

FIG. 6A and FIG. 6B are graphs for describing the difference in seal performance between a slide device according to an experimental example and a slide device for comparison. FIG. 6A is a graph showing a result of measurement of leakage amount of physiological salt solution in the slide device for comparison, and FIG. 6B is a graph showing a result of measurement of leakage amount of physiological salt solution in the slide device according to the experimental example. In the graphs shown in FIG. 6A and FIG. 6B, a leakage amount of physiological salt solution is taken on an axis of ordinates, and a time elapsed from starting of the experiment is taken on axis of abscissas. In the graphs, a leakage amount of physiological salt solution is described later, and is abbreviated as "leakage amount" in the graphs, and a unit of the leakage amount is ml. The time lapsed from starting the experiment is abbreviated as "lapsed time" in the graphs, and a unit of the lapsed time is hour.

In the experimental example 1, seal performance is compared between the slide device for comparison which is a conventional slide device and the slide device according to the experimental example which is the slide device according to the present invention.

First, the slide device according to the experimental example and the slide device for comparison are described.

The slide device according to the experimental example basically has substantially the same configuration as the configuration of the slide device 1 according to the embodiment 1. A size of a gap on the innermost periphery of an opposedly facing region is set to 0.5 μm.

A fixed-side slide member is made of silicon carbide.

An outer diameter of a first slide surface is set to 11.0 mm and an inner diameter of the first slide surface is set to 8.0 mm. The first slide surface is formed in a shape where the more the first slide surface extends toward the outer peripheral side, the more the first slide surface projects toward the second slide surface. An arithmetic average surface roughness of the first slide surface is set to a value which falls within a range of from 0.05 μm to 0.10 μm. Flatness of the first slide surface is set to 0.5 μm (the highest point disposed at the outermost periphery and the lowest point disposed on the innermost periphery).

A rotary-side slide member is made of carbon.

An outer diameter of a second slide surface is set to 11.0 mm and an inner diameter of the second slide surface is set to 8.2 mm. The second slide surface is formed in a flat surface shape perpendicular to the axis of rotation of the rotary-side slide member. An arithmetic average roughness of the second slide surface is set to 0.25 μm or less. Flatness of the second slide surface is set to 0.3 μm (the highest point and the lowest point not defined).

The slide device for comparison basically has substantially the same configuration as the configuration of the slide device according to the experimental example. However, the slide device for comparison differs from the slide device according to the experimental example in the configuration of the first slide surface. That is, in the slide device for comparison, the first slide surface is formed in a flat surface shape perpendicular to the axis of rotation of the rotary-side slide member. Flatness of the first slide surface in the slide device for comparison is set to 0.3 μm (the highest point and the lowest point not defined).

An experiment is carried out by assembling the slide device according to the experimental example and the slide device for comparison into blood pumps (pumps substantially equal to blood pumps used for medical use) having the same configuration respectively. The configuration of the blood pump is substantially equal to the blood pump 110 according to the embodiment 1 except for the slide device and hence, the detailed description of the configuration of the blood pump is omitted. Hereinafter, the blood pump into which the slide device according to the experimental example is assembled is referred to as "blood pump according to experimental example", and the blood pump into which the slide device for comparison is assembled is referred to as "blood pump for comparison".

Next, experimental conditions and the like for the experimental example 1 are described.

In the experimental example 1, the blood pump is operated in a state where a flow passage through which a liquid containing a blood component in the blood pump flows (hereinafter referred to as blood flow path) is filled with physiological salt solution and a liquid circulation path is filled with pure water. Physiological salt solution is made to circulate in the blood flow path by an impeller, and pure water is made to circulate in the liquid circulation path by an externally mounted circulation device. In such a state, a change in electric conductivity of pure water is measured, and an amount of physiological salt solution which enters (leaks to) an inner peripheral side of a slide member is calculated based on the change in electric conductivity.

The liquid circulation path is disposed just on an inner peripheral side of the slide device (see symbols 40, 46 in FIG. 3). Accordingly, when physiological salt solution which is assumed as a blood enters the inner peripheral side of the slide device, salt is mixed into pure water so that electric conductivity changes. Accordingly, by tracing a change in electric conductivity, an amount (leakage amount) of a physiological salt solution which enters the inner peripheral side of the slide member can be calculated based on a volume and electric conductivity of pure water, and salt concentration in physiological salt solution (0.9 wt %).

In the experimental example 1, 500 ml of physiological salt solution and 500 ml of pure water are used. A change in electric conductivity is measured using a conductivity meter. In this experimental example 1, a Multi Water Quality Meter MM-60R made by DKK-TOA CORPORATION and immersion-type electric conductivity cell "Cal-Memo" R-Series, CT-57101B for general use made by DKK-TOA CORPORATION are used in combination as the conductivity meter. A rotational speed of a rotary drive part is set to 2200 rpm. A water temperature (a temperature of a liquid for experiment) is set to a room temperature. A load (pressing force) applied to a fixed-side slide member and a rotary-side slide member is set to 200 gf.

Next, a result of the experimental example 1 is described.

As shown in FIG. 6, a leakage amount in the slide device according to the experimental example (see FIG. 6B) is smaller than a leakage amount in the slide device for comparison (see FIG. 6A).

To calculate a leakage amount per day (24 hours) based on the result of the experiment, the leakage amount is 0.101 ml/day in case of the slide device for comparison, and is 0.016 ml/day in case of the slide device according to the experimental example.

Accordingly, it is confirmed that the slide device according to the present invention is a slide device capable of having higher seal performance than the conventional slide device.

Experimental Example 2

Figure 7:
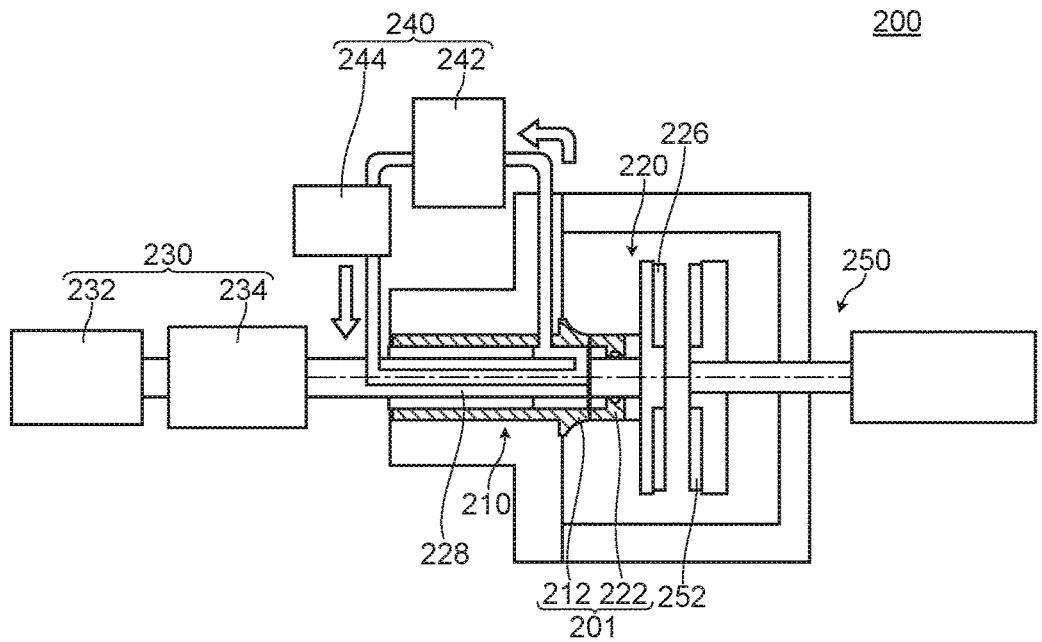
FIG. 7 is a view showing an experimental device 200 used in an experimental example 2.

FIG. 7 is a view showing an experimental device 200 used in the experimental example 2. In FIG. 7, a slide device 201 and the like are shown in cross section, and a rotary drive part 230 and the like are schematically shown.

Figure 8A:
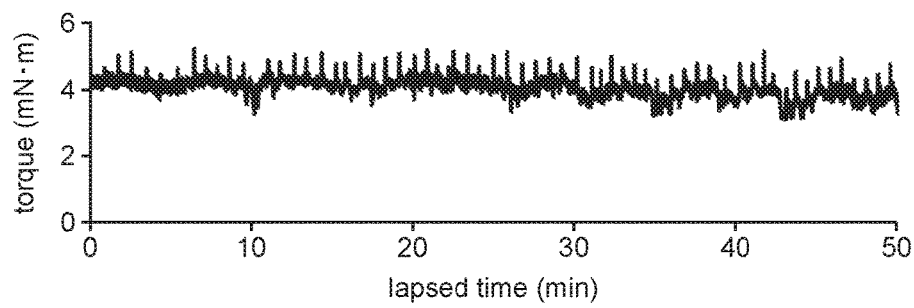
FIG. 8A and FIG. 8B are graphs for describing the difference in slide resistance between a slide device according to an experimental example and a slide device for comparison.
Figure 8B:
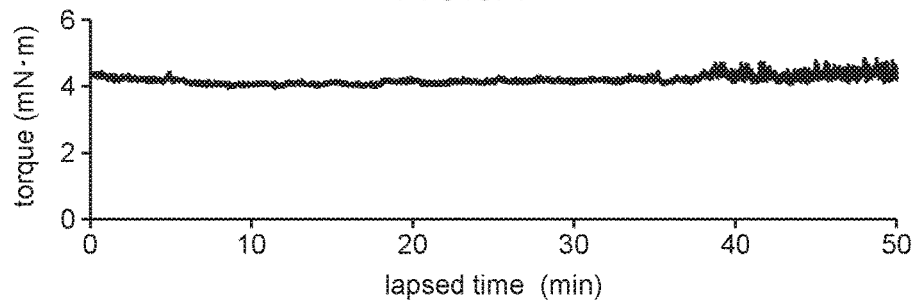
Figure 9A:
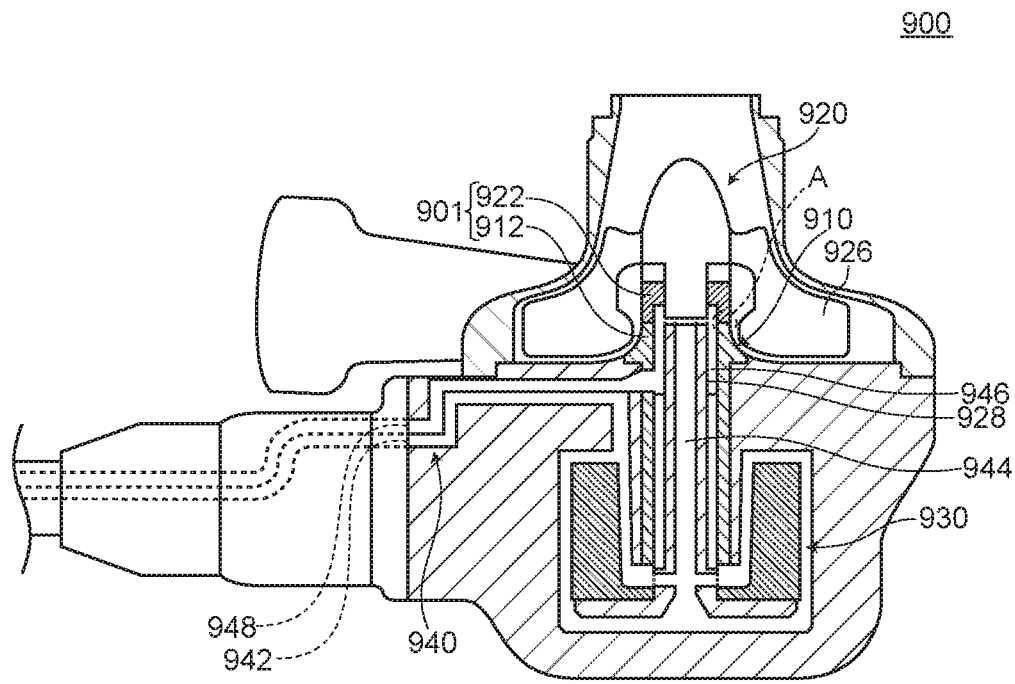
FIG. 9A and FIG. 9B are cross-sectional views of a conventional blood pump 900.
Figure 9B:
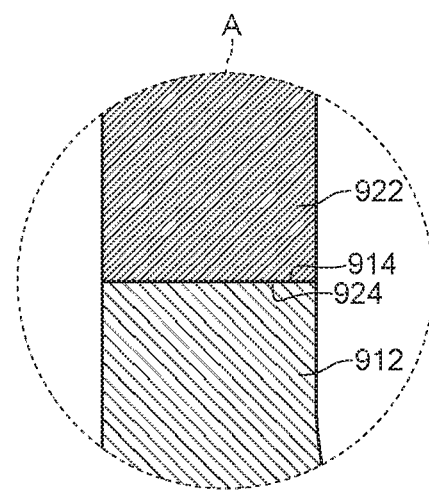

FIG. 8A and FIG. 8B are graphs for describing the difference in slide resistance between the slide device according to the experimental example and a slide device for comparison. FIG. 8A is a graph showing a mode of a torque of a rotary motor in the slide device for comparison, and FIG. 8B is a graph showing a mode of a torque of a rotary motor in the slide device according to the experimental example 2. In FIG. 8A and FIG. 8B, the torque of the rotary motor is taken on an axis of ordinates, and a time elapsed from starting the experiment is taken on an axis of abscissas. The torque of the rotary motor is abbreviated as "torque" in the graph and a unit of the torque is mN·m. The time elapsed from starting the experiment is abbreviated as "elapsed time" in the graph, and a unit of elapsed time is a minute.

In the experimental example 2, stability of slide resistance is compared between the slide device for comparison which is a conventional slide device and the slide device according to the experimental example 2 which is the slide device according to the present invention.

In the experimental example 2, as the slide device according to the experimental example and the slide device for comparison, slide devices substantially equal to the slide devices used in the experimental example 1 are used.

In the experimental example 2, the slide device according to the experimental example and the slide device for comparison are assembled into an experimental device 200 described hereinafter. The reason the experimental device 200 is used is that a torque detecting part (torque meter) cannot be assembled into a blood pump.

The experimental device 200 has the structure similar to the structure of the blood pump 110 according to the embodiment 1, and includes a fixing part 210, a rotary part 220, a rotary drive part 230, a liquid circulation path 240, and a load adjusting part 250.

The fixing part 210 includes a fixed-side slide member 212. The fixed-side slide member 212 has a first slide surface 214 (symbol not shown in the drawing).

The rotary part 220 includes: a rotary-side slide member 222; a magnet 226; and a rotary shaft 228. The rotary-side slide member 222 has a second slide surface 224 (symbol not shown in the drawing). The magnet 226 is used for applying a load between the fixed-side slide member 212 and the rotary-side slide member 222 by making use of a repulsive force generated between the magnet 226 and a magnet 252 in the load adjusting part 250.

The rotary drive part 230 includes a rotary motor 232 and a torque detecting part 234, and rotates the rotary part 220 by way of the rotary shaft 228. The torque detecting part 234 includes a torque meter (TH-3203 made by ONO SOKKI CO., LTD).

The liquid circulation path 240 includes a tank 242 and a pump 244. The liquid circulation path 240 shown in FIG. 7 schematically expresses the flow of pure water, and does not directly express an actually used equipment (water pipe or the like).

The load adjusting part 250 is provided for applying a load to the fixed-side slide member 212 and the rotary-side slide member 222. The load adjusting part 250 includes the magnet 252. The magnet 252 opposedly faces the magnet 226 of the rotary part 220 having the same polarity as the magnet 252.

The fixed-side slide member 212 and the rotary-side slide member 222 form the slide device 201. An experiment is carried out by assembling the slide device according to the experimental example or the slide device for comparison into the experimental device 200 as the slide device 201.

Next, experimental conditions and the like for the experimental example 2 are described.

In the experimental example 2, the experimental device 200 is operated in a state where an outer peripheral side of the slide device 201 is filled with blood of a pig and the liquid circulation path 240 is filled with pure water, and a mode of a torque of a rotary motor is observed.

When resistance is applied to the slide device, a load is applied to the rotary motor so that a rotational speed of the rotary motor is decreased. An auxiliary artificial heart system includes a feedback mechanism for setting a rotational speed of the rotary motor at a fixed value as much as possible and hence, when the rotational speed is decreased, a torque of the rotary motor is increased so as to restore the rotational speed. Accordingly, stability of slide resistance can be evaluated by observing a mode of a torque of the rotary motor.

In the experimental example 2, 100 ml of blood of a pig (containing 15% of ACD-A solution and one bottle of GENTACIN Injection 40 per 1 L (made by MSD Ltd)) and 500 ml of pure water are used. A rotational speed of the rotational part is set to 2000 rpm. A water temperature (a temperature of a liquid for the experiment) is set to 37° C. A load (pressing force) applied to the fixed-side slide member and the rotary-side slide member is set to 2N.

Next, a result of the experimental example 2 is described.

When the slide device for comparison is assembled into the experimental device 200, an instantaneous elevation of a torque is periodically observed (see FIG. 8A). On the other hand, when the slide member according to the experimental example is assembled into the experimental device 200, an instantaneous elevation of a torque is not recognized so that the experimental device 200 exhibits stable behavior (see FIG. 8B).

Accordingly, it is confirmed that, with the use of the slide device of the present invention, slide resistance can be made more stable compared to the conventional slide device.

Although the present invention has been described based on the above-mentioned embodiments heretofore, the present invention is not limited to the above-mentioned embodiments. The present invention can be carried out in various modes without departing from the gist of the present invention, and for example, the following modifications are also conceivable.

(1) The numbers, materials, shapes, positions, sizes and the like of the constitutional elements described in the above-mentioned respective embodiments are provided only for an exemplifying purpose, and can be changed within a scope where advantageous effects of the present invention are not impaired.

(2) In the above-mentioned embodiments 1 and 2, the slide surface which is formed in a shape where the more the slide surface extends toward the outer peripheral side, the more the other slide surface projects toward one slide surface is the first slide surface. However, the present invention is not limited to such a configuration. The second slide surface may be the slide surface which is formed in a shape where the more the other slide surface extends toward the outer peripheral side, the more the other slide surface projects toward one slide surface.

(3) In the slide device of the present invention, "affinity treatment" which is the treatment for forming a hydrate of silicon oxide on a slide surface may be applied to the slide member made of silicon carbide before the slide member is assembled to the slide device. With such a configuration, the slide surface of the slide member made of silicon carbide has "a hydrate of silicon oxide having high hydrophilicity" due to a tribochemical reaction. Accordingly, "a blood component having hydrophobicity" minimally adheres to the slide surface. As a result, when the slide member is used in an aqueous liquid containing a blood component, slide resistance can be reduced compared to a conventional slide device.

REFERENCE SIGNS LIST 1, 2, 201, 901: slide device
110, 900: blood pump
10, 50, 210, 910: fixed part
12, 52, 212, 912: fixed-side slide member
14, 54, 914: first slide surface
20, 220, 920: rotary part
22, 222, 922: rotary-side slide member
24, 924: second slide surface
26, 926: impeller
28, 228, 928: rotary shaft
30, 330: rotary drive device
32: blood pump chamber
40, 240: liquid circulation path
100: auxiliary artificial heart system
120, 130: artificial blood vessel
140: cable
200: experimental device
226, 252: magnet
232: rotary motor
234: torque detecting part
242: tank
244: pump
250: load adjusting part
a: axis of rotation of rotary-side slide member
d: size of gap on innermost periphery
S: gap

The invention claimed is:

1. A slide device comprising:
   a fixed-side slide member having an annular-shaped first slide surface; and
   a rotary-side slide member having an annular-shaped second slide surface, wherein the slide device is configured to be used in a state where the first slide surface and the second slide surface are made to oppositely face each other, and an outer peripheral side of the fixed-side slide member and an outer peripheral side of the rotary-side slide member are brought into contact with a liquid containing a blood component, wherein
   assuming a region where the first slide surface and the second slide surface oppositely face each other as viewed in a direction along an axis of rotation of the rotary-side slide member as an oppositely facing region, the first slide surface and the second slide surface are brought into contact with each other on an outermost periphery of the oppositely facing region.

2. The slide device according to claim 1, wherein a gap is formed between the first slide surface and the second slide surface on an inner peripheral side of a contact position where the first slide surface and the second slide surface are brought into contact with each other, a size of the gap being increased as a distance toward the inner peripheral side from the contact position is increased, and
   to express the size of the gap at an innermost periphery of the oppositely facing region along a direction parallel to the axis of rotation of the rotary-side slide member, the size of the gap at the innermost periphery is set to a value which falls within a range of from 0.2 μm to 0.8 μm.

3. The slide device according to claim 2, wherein an arithmetic average roughness of the first slide surface and an arithmetic average roughness of the second slide surface are set smaller than the size of the gap on the innermost periphery.

4. The slide device according to claim 1, wherein one slide surface out of the first slide surface and the second slide surface is formed in a flat surface shape perpendicular to the axis of rotation of the rotary-side slide member, and the other slide surface out of the first slide surface and the second slide surface is formed in a shape where the more the other slide surface extends toward the outer peripheral side, the more the other slide surface projects toward said one slide surface.

5. The slide device according to claim 1, wherein the first slide surface is formed in a shape where the more the first slide surface extends toward the outer peripheral side, the more the first slide surface projects toward the rotary-side slide member, and the second slide surface is formed in a shape where the more the second slide surface extends toward the outer peripheral side, the more the second slide surface projects toward the fixed-side slide member.

6. The slide device according to claim 1, wherein at least one slide member out of the fixed-side slide member and the rotary-side slide member is made of silicon carbide.

7. The slide device according to claim 1, wherein the slide device is a slide device which is used in a state where a predetermined liquid is made to pass on an inner peripheral side of the fixed-side slide member and on an inner peripheral side of the rotary-side slide member.

8. The slide device according to claim 1, wherein antithrombotic treatment is applied to an outer periphery of the fixed-side slide member and an outer periphery of the rotary-side slide member.

9. A mechanical seal equipped with the slide device according to claim 1.

10. A pump equipped with the mechanical seal according to claim 9.

11. The pump according to claim 10, wherein the pump is a blood pump.

12. An auxiliary artificial heart system equipped with the blood pump according to claim 11.

* * * * *